United States Patent [19]
Miller et al.

[11] Patent Number: 5,868,140
[45] Date of Patent: *Feb. 9, 1999

[54] SURGICAL METHOD AND APPARATUS FOR IMPLANTATION OF A TESTICULAR PROSTHETIC DEVICE

[75] Inventors: Gregg A. Miller, Buckner; R. Duane Holder, Independence, both of Mo.

[73] Assignee: CTI Corporation, Buckner, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 689,607

[22] Filed: Aug. 12, 1996

Related U.S. Application Data

[63] Continuation-in-part of Ser. No. 46,172, Nov. 7, 1995, abandoned.

[51] Int. Cl.$^6$ ................................................. A61B 19/00
[52] U.S. Cl. ............................................. 128/898; 623/11
[58] Field of Search ..................... 623/8, 11, 66; 128/898, 25; 600/40; 606/135

[56] References Cited

U.S. PATENT DOCUMENTS

| | | | |
|---|---|---|---|
| 4,009,711 | 3/1977 | Uson | 600/40 |
| 4,201,202 | 5/1980 | Finney et al. | 600/40 |
| 4,267,829 | 5/1981 | Burton et al. | 600/40 |
| 5,141,581 | 8/1992 | Markham | 156/242 |
| 5,282,857 | 2/1994 | Perry et al. | 623/8 |
| 5,344,451 | 9/1994 | Dayton . | |
| 5,531,786 | 7/1996 | Perry et al. | 623/8 |

OTHER PUBLICATIONS

Gilbert, M et al. "Artificial Testicles in Children." South Med J 62(5):611–4, May 1969.
Mentor Corporation product information for Mentor Heyer–Schulte Testicular Prostheses, Jun. 1984.
Beer, M. et al. "Testicular Protheses." Urological Clinics of North America 16(1):133–138, Feb. 1989.
Ortenberg, J et al. "The How and Why of Synthetic Replacement Testicles." Contemporary Urology: pp. 23–32, Oct. 1991.
Neuticles WWW Web site http://www.webpost.net/neuticles/Tp02.htm, 1997.
*Endocrinology* (United States), May 1995, 136, pp. 1969–1977, Majumdar SS, Mikuma N, Ishwad PC, Winters SJ, Attardi BJ, Perera AD, and Plant TM, Authors.
*Endocrinology Journal* (England), Jun. 1994, 41 (3), pp. 257–265, Takikawa M, and Wakabayashi K, Authors.
*Human Reproduction* (England), Mar. 1994 9 (3), pp. 463–470, Hendry WF, Parslow JM, Parkinson MC, and Lowe DG, Authors.
*Endocrinology* (United States), Sep. 1993, 133 (3), pp. 1173–1181, Tena–Sempere M, Pinilla L, and Aguilar E, Authors.

(List continued on next page.)

*Primary Examiner*—David H. Willse
*Assistant Examiner*—Kelly O'Hara
*Attorney, Agent, or Firm*—Sixbey, Friedman, Leedom & Ferguson; Frank P. Presta; Joseph S. Presta

[57] ABSTRACT

A method and apparatus for implanting a testicular prosthetic device includes creating a passageway into the interior of an animal's scrotum which contains a tunica vaginalis; incising the tunica vaginalis containing a testis attached to a spermatic cord; severing the spermatic cord; removing the testis through the passageway and inserting a prosthetic device through the passageway and into the lumen of the tunica and closing the tunica. The second testis is similarly removed from its tunica vaginalis through the same passageway and a similar prosthetic device is placed in the cavity created. The tunica may be drawn outwardly, thought the passageway, and removal of the testis by incising the tunica and severing the spermatic cord may be performed outside the animal. The tunica may also be severed and the prosthetic device placed directly within the scrotal sac. The testicular implant is generally kidney-shaped and is sized to fit the tunica.

15 Claims, 2 Drawing Sheets

OTHER PUBLICATIONS

*Boletin Medico Del Hospital Infanta De Mexico* (Mexico), Aug. 1993, 50 (8), pp. 590–595, Orozco–Sanchez J, Samano–Martinez A, and Neri–Vela R, Authors.

*Radiotherapy and Oncology* (Netherlands), Nov. 1992, 25 (3), pp. 207–212, Tinkler SD, Howard GC, and Kerr GR, Authors.

*European Journal of Pharmacology* (Netherlands), Apr. 1992, 215 (1), pp. 99–107, Wilson MA and Biscardi R, Authors.

*Neuroendocrinology* (Switzerland), Jul. 1992, 56 (1), pp. 85–93, Aguilar E, Rodriguez Padilla ML, Bellido C, Tena–Sempere M, and Pinilla L, Authors.

*Annales Urologique* (France), 1992, 26 (2), pp. 80–82, Auberget JL and Vautherin R, Authors.

*Life Sciences* (England), 1991, 49 (15), pp. 1073–1077, Arslan M, Rizvi SS, Jahan S, Zaidi P, and Shalab M, Authors.

*Endocrinology* (United States), Aug. 1991, 129 (2) pp. 877–882, Aguila–Mansilla N, Kedzierski W, and Porter JC, Authors.

*Endocrinology* (United States), May 1991, 128 (5), pp. 2407–2414, Viger RS, and Robaire B, Authors.

*Acta Endocrinologica* (Denmark), Apr. 1990, 122 (4), pp. 432–442, Weinbauer GF, Jackwerth B, Yoon YD, Behre HM, Yeung CH, and Nieschlad E, Authors.

*Biology of Reproduction* (United States), Mar. 1989, 40 (3), pp. 578–584, Abeyawardene SA, and Plant TM, Authors.

*Neuroendocrinology*, (Switzerland), Apr. 1989, 49 (4), pp. 395–401, Arslan M, Weinbauer GF, Khan SA and Nieschlag E, Authors.

*Biology of Reproduction* (United States), Jun. 1987, 36 (5), pp. 1142–1148, Schanbacher BD, Fletcher PW and Reichert LE Jr., Authors.

*Zeitschrift fur Urologie und Nephrologie* (Germany East), Mar. 1987, 80 (3), pp. 135–138, Stahl F, Schnoor D, Rohde W, and Dorner G, Authors.

*Journal of Endocrinology* (England), Mar. 1987, 112 (3), pp. 345–350, Greenstein BD, Fitzpatrick FT, Kendall MD, and Wheeler MJ, Authors.

*Annals of the Academy of Medicine, Singapore,* (Singapore), Jan. 1986, 15 (1), pp. 122–126, Lim SM, Author.

*Biology of Reproduction* (United States), Nov. 1983, 29 (4), pp. 819–823, Johnson LM and Gay VL, Authors.

*American Journal of Physiology* (United States), Nov. 1982, 243 (5), pp. R546–R551, Zucker I and Boshes M, Authors.

*Biology of Reproduction* (United States), May 1982, 26 (4), pp. 559–565, Robaire B and Hales BF, Authors.

*Endocrinology* (United States), Jun. 1982, 110 (6), pp. 1905–1913, Plant TM, Author.

*Comptes Rendus des Seances de l'Academie des sciences, serie 3, Sciences de la Vie* (France), Nov. 1981, 293 (10), pp. 589–594, Fournier–Delpach S, Pisselet C, Garnier DH, Dubois M and Courot M, Authors.

*Journal of Endocrinology* (England), Oct. 1981, 91 (1), pp. 75–79, Gogan F, Slama A, Bizzini–Koutznetzova B, Dray F and Kordon C, Authors.

*Archives of Andorlogy* (United States), May 1978, 1 (3), pp. 257–266, Gay VL and Kerlan JT, Authors.

*European Urology* (Switzerland), 1976, 2 (2), pp. 85–88, Schnorr D, Mebel M, Dorner G, Stahl F and Rohde W, Authors.

SURGICAL METHOD AND APPARATUS FOR IMPLANTATION OF A TESTICULAR PROSTHETIC DEVICE

CROSS REFERENCE TO RELATED APPLICATION

This application is a continuation-in-part of design U.S. patent application Ser. No. 29/046,172 filed Nov. 7, 1995, now abandoned entitled CANINE TESTICULAR IMPLANT. The subject matter of the parent application is expressly incorporated herein by reference.

FIELD OF THE INVENTION

The present invention is broadly concerned with a method and apparatus for implanting a testicular prosthetic device which provides for insulation of the prosthesis against abrasion and injury and minimizes postoperative swelling of the surrounding tissues. More particularly, it is concerned with a method in which a passageway is created into the interior of the scrotum of an animal such as a dog or a cat or the like; a tunica vaginalis is incised and a testis therein is removed and replaced with a prosthetic device; and the tunica is closed. The second testis is similarly removed from its tunica vaginalis through the same passageway and a similar prosthetic device is placed in the cavity created. In this manner, both testes are removed and replaced with prosthetic devices. The generally kidney-shaped testicular implant of the invention is constructed of an appropriate size to fit snugly within the tunica.

BACKGROUND OF THE INVENTION

In order to control population growth, it is commonly recommended that animals not kept for breeding purposes be neutered. Unrestricted breeding among animals leads to overpopulation, particularly of "stray" or abandoned animals. In metropolitan areas, such overbreeding necessitates costly animal control programs to maintain public health and control nuisances. To avoid such problems, neutering is particularly encouraged for small animals kept as household pets, such as dogs and cats. In male animals, this is accomplished by orchidectomy, or surgical removal of the testes from the scrotal sac.

Such surgery is generally safe for the animal and relatively inexpensive. However, the surgery does alter the appearance of the animal. In large dogs, such as bloodhounds, mastiffs and shepherds, the empty scrotal sac is particularly noticeable. While recognizing that responsible pet ownership requires neutering, nonetheless, many pet owners find themselves uncomfortable with such a disfiguring procedure. The permanently altered appearance of their pet serves as a constant reminder of their surgical choice. Comments by strangers who misidentify the gender of the pet may serve to exacerbate this discomfort.

SUMMARY OF THE INVENTION

The present invention overcomes the problems outlined above and provides a method and apparatus for implanting a prosthetic device which provides for insulation of the prosthesis against abrasion and injury and minimizes postoperative swelling of the surrounding tissues. Broadly speaking, the method includes creating a passageway into the interior of an animal's scrotum which contains a tunica vaginalis, incising the tunica vaginalis containing a testis attached to a spermatic cord, severing the spermatic cord, removing the testis through the passageway and inserting a prosthetic device through the passageway and into the lumen of the tunica vaginalis, and closing the tunica. The second testis is removed through the same passageway. Another preferred embodiment which is particularly well-adapted to implantation of a prosthesis where the testes have previously been removed, involves creating a passageway into the interior of the scrotum, severing the tunica vaginalis containing the spermatic cord and testis at a point above the testis, removal of the testis through the passageway and placement of a prosthetic device within the scrotal sac. The procedure is repeated for the second testis.

In particularly preferred methods the tunica containing the testis and attached spermatic cord is drawn outwardly, through the passageway, and removal of the testis, by incising the tunica and severing the spermatic cord, or by severing both the tunic and cord, is performed outside the animal. The preferred prosthetic device is a solid, light weight, generally kidney-shaped device.

OBJECTS AND ADVANTAGES OF THE INVENTION

The principal objects and advantages of the present invention include providing a method and device which permit reconstruction of the external appearance of an animal prior to orchidectomy; providing a method which insulates an implanted testicular prosthesis against abrasion and injury; providing such a method which minimizes postoperative swelling of the surrounding tissues; providing such a method which is particularly well-adapted to ensure that the implanted prosthesis remains in place; providing a method which permits implantation of a prosthesis at the time of removal of a testis or later, following a previous orchidectomy; providing such a method and device which are both economical and safe for the animal; providing such a device which is nontoxic and will not be rejected by the animal; and providing such a method which minimizes the extent of the wound.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE PREFERRED EMBODIMENTS

1. Introduction and Environment

Figure 1:
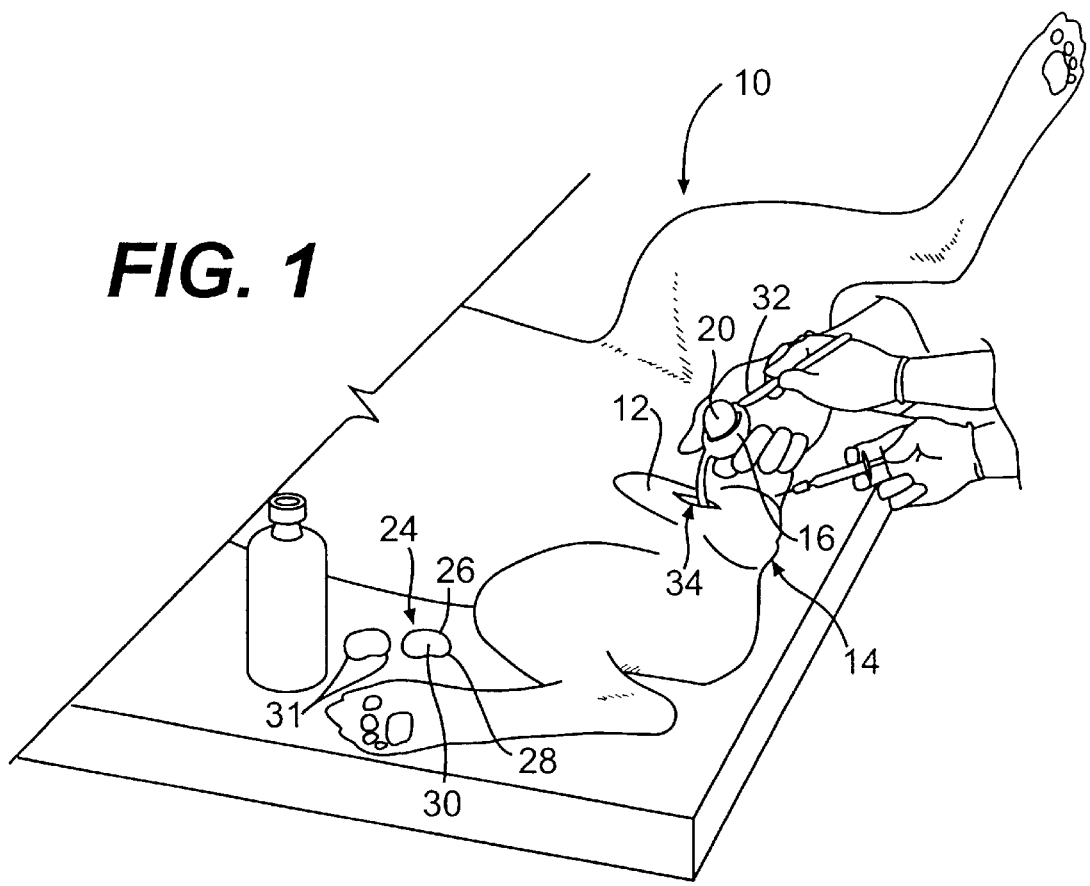
FIG. 1 is a right side perspective view of a dog showing the spermatic cord and attached tunic opened to remove the testis in the method of the invention.

As required, detailed embodiments of the present invention are disclosed herein, however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The method of the invention is preferably employed for surgical removal of the testes and implantation of prosthetic devices for small animals, such as dogs and cats. However, it can be effectively employed on any suitable mammalian species.

In preferred methods, the animal is first tranquilized using a suitable preanesthetic drug such as promazine hydrochloride, and then anesthetized, using a general anesthetic, such as pentobarbital, halothane, or any of a number of other suitable preparations. A tiltable operating table may be employed and may be tilted so as to elevate the surgical field to a convenient height for the operating surgeon. The animal is then prepared for surgery by clipping the fur from site of the incision and a wide area of adjacent skin. Full sterile surgical technique is preferred, and the site is cleaned sequentially with a soap solution, and one or more antiseptic solutions such as alcohol, and merthiolate. A sterile drape is positioned to permit visualization of the operating field. The prosthetic device is preferably sterilized in an autoclave, although gas sterilization or cold sterilization may also be employed. In certain preferred methods a broad spectrum antibiotic may be injected into the scrotal area following the surgery, to forestall growth of bacteria caused by licking of the wound area.

2. Tunical Implantation

Referring now to the drawings, an animal such as a dog or the like, having a pelvic area 10, which is the functional region of a testicular implantation procedure, is depicted in dorsal recumbent position. Certain parts of the pelvic area include the skin 12, scrotum 14, septum scroti 15, and tunica vaginalis 16 containing the spermatic cord 18, and testis 20. The testes 20 are suspended in the scrotum 14 by the spermatic cords 18. It is understood that the area as shown includes fascia, ligaments, nerves, blood vessels, fat and other anatomical structures not depicted for purposes of clarity.

The prosthetic device 24 employed in accordance with the invention is generally kidney shaped, having a convex border 26, and a concave border 28, punctuated by a central cleft 30, between a pair of lobes 31. The size of the device 24 is such that it fits snugly within the tunica 16. The implant 24 is formed of a biologically inert synthetic resin, such as polypropylene, polyethylene, or polystyrene, or any similar substance which is lightweight, inert and economical to manufacture. In certain preferred embodiments, the implant includes an externally detectable member, such as a piece of metal or magnetic code.

Figure 2:
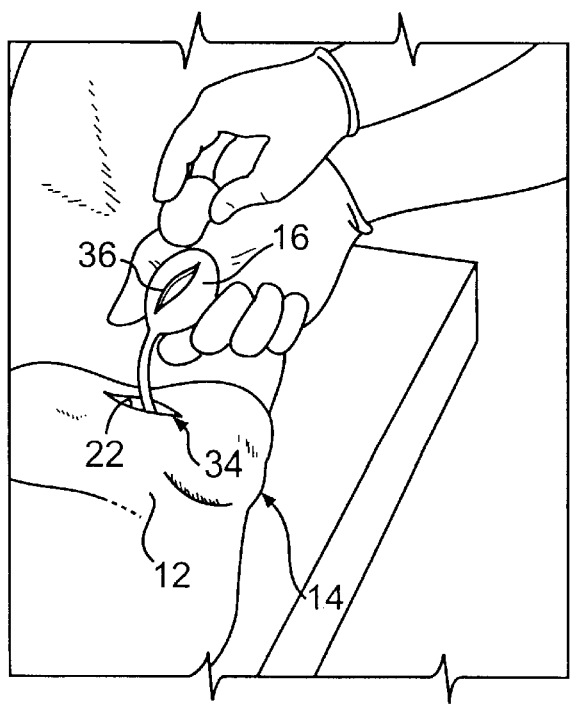
FIG. 2 is an enlarged detail portion of FIG. 1 depicting placement of a prosthetic device in the lumen of the tunic.

As illustrated in FIGS. 1 and 2, the animal is positioned supine, in the dorsal recumbent position, with the rear legs stretched or tied. A scalpel 32 is employed to make a midline prescrotal incision 34 of from about one half inch to about one and one half inches in length, depending on the size of the testis to be removed therethrough. The incision may be made anterior to the scrotum 14 or it may be made generally adjacent the base of the scrotum. In preferred methods, one of the animal's testes 20 is pushed toward the incision 34 to facilitate the procedure. The incision is deepened through the subcutaneous tissue and spermatic fascia, to create a passageway 22 to the parietal vaginal tunic 16, the serous covering of the testis 20. The tunica 16 containing the testis 20, attached epididymis (not shown), and spermatic cord 18 are pushed through the incision 34, to the exterior of the animal. The spermatic fascia and scrotal ligament close to the testis 20 are incised to free the exposed tunica 16 containing the testis 20 from its scrotal attachment. In certain preferred methods, fat and fascia surrounding the parietal vaginal tunic 16 may be reflected proximally with a gauze sponge to permit maximum exteriorization of the spermatic cord 18 and testis 20.

Figure 4:
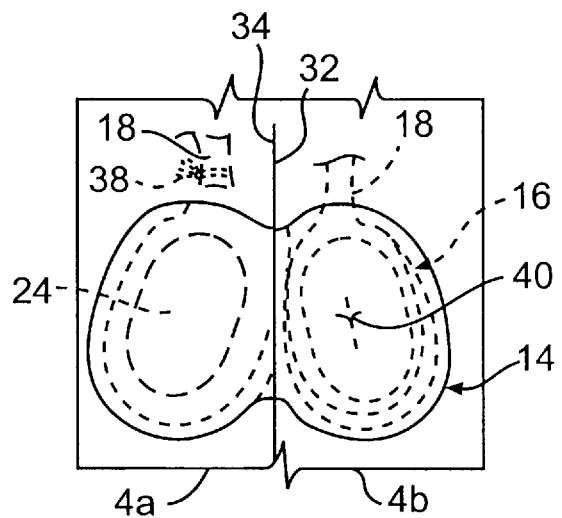
FIG. 4 is an enlarged, composite, partial top plan view of the surgical area depicted in FIG. 1, 4a showing a prosthesis in place in the scrotal sac, and 4b showing a prosthesis in place in the lumen of the tunica within the scrotal sac.

As best shown in FIGS. 2 and 4b, an incision 36 is made through the tunica large enough to permit removal of the testis 20. The testis is removed, the spermatic cord 18 is ligated, its connection to the testis 20 is severed, at ligature 38 and the prosthetic device is inserted in the tunica so that the convex surface 26 faces anterior or forward and slightly downward, and the concave surface 28 containing cleft 30 and lobes 31 faces posterior or backward and slightly upwardly. Following placement of the prosthesis, the edges of the tunica are reapproximated and closed by a suture 40. In preferred embodiments an absorbable chromic gut ligature is employed. The tunica 16 containing the prosthetic device 24 is then pushed back through passageway 22 and into the scrotum 14.

Entering through the same incision to the other side of the septum scroti 15 which divides the scrotum 14 into a pair of cavities 15a,b, one for each of the two testes, the remaining testis 20 may be removed and a second prosthetic device 24 placed in the same manner and then replaced on the respective side of the septum 15.

Following placement of the second prosthesis, the prescrotal incision 34 may optionally be sutured closed with a nonabsorbable skin suture 42 such as nylon. However, since the weight of the implant 24 serves to retain the implant in a pendant position within the scrotum, suturing of the incision 34 is not generally required. In cases where the animal is likely to lick the wound so vigorously as to reopen the incision, surgical steel wire suture may be employed to suture the incision.

3. Scrotal Implantation

Figure 3:
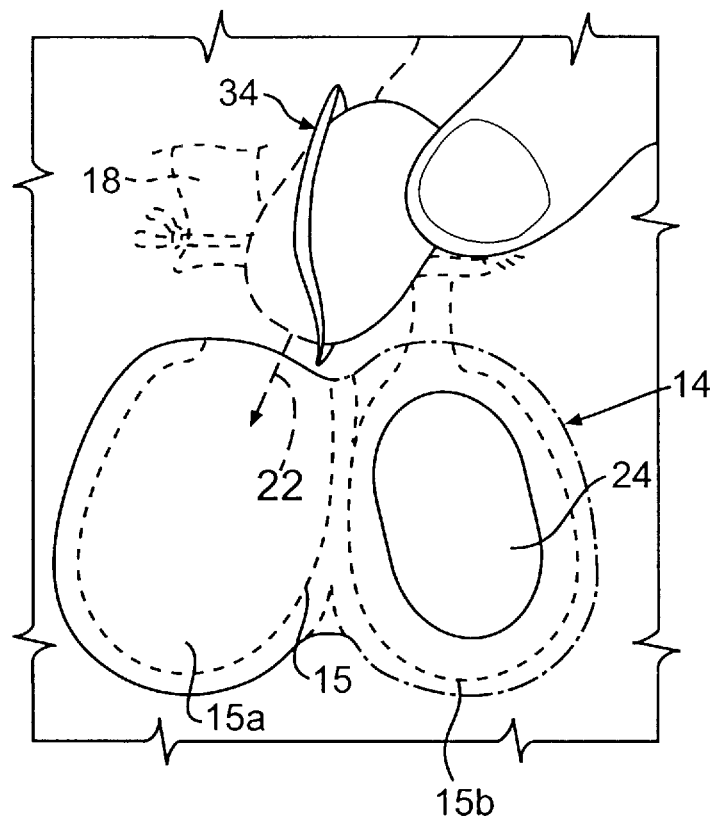
FIG. 3 is an enlarged partial top plan view of the surgical area of FIG. 1, showing the ligated spermatic cord in phantom and insertion of a prosthesis into the scrotal sac according to an alternate method of the invention.

In other preferred embodiments, the prosthetic device 24 may be implanted directly into the scrotum 14. The procedure is similar to that previously described for tunical implantation. As best shown in FIGS. 3 and 4a, a prescrotal incision 34 is made and deepened to create a passageway 22 to the parietal vaginal tunic 16. The spermatic fascia and scrotal ligament are incised to free the exposed tunica 16 containing the testis 20 from its scrotal attachment. The tunica 16 containing the testis 20 and attached spermatic cord 18 is pushed through the incision 34 to the exterior of the animal.

The exteriorized tunic 16 and underlying spermatic cord 18 are ligated and transected and the tunica, cord and all subjacent parts, including the testis are discarded, and the prosthesis 24 is placed in the scrotal sac.

In an alternate preferred method, the tunica 16 and spermatic cord 18 are separately ligated and transected. In still another alternate preferred method, the tunica 16 is incised prior to exteriorization, the tunica 16 is dissected away from the remainder of the spermatic cord 18 and the two are transected independently.

Following transection, the stump of the extended spermatic cord 18 is released for retraction back through the inguinal canal, well away from the now empty the scrotal sac 14.

Entering through the same incision to the other side of the septum scroti 15, the remaining testis 20 may be removed and a second prosthetic device 24 placed in the same manner. In such a scrotal placement, the septum scroti 15 keeps the implants separated.

It is to be understood that while certain forms of the present invention have been illustrated and described herein, it is not to be limited to the specific forms or arrangement of parts described and shown.

What is claimed and desired to be secured by Letters Patent is as follows:

1. A method for neutering a quadruped animal, said method comprising the steps of:
   (a) creating a passageway into the interior of the animal's scrotum which contains a tunica vaginalis, a spermatic cord and a testis by incising the prescrotal skin;
   (b) incising the tunica vaginalis in the lumen thereof;
   (c) severing the spermatic cord and removing the testis through said passageway;
   (d) inserting a prosthetic device through said passageway and into the lumen of the tunica vaginalis; and
   (e) closing the tunica.

2. The method as set forth in claim 1, and further including the steps of
   (f) repeating steps b, c, d and e to remove a second testis and implant a second prosthetic device.

3. The method as set forth in claim 1, and further including the step of closing the passageway.

4. The method as set forth in claim 1, wherein the scrotum presents an anterior portion and a posterior portion, the prosthetic device is generally kidney shaped, presenting a convex surface and a concave surface, and further including the step of:
   (f) the prosthetic device being inserted with the convex surface facing the anterior portion of the scrotum and the concave surface facing the posterior portion of the scrotum.

5. The method as set forth in claim 1, the animal being selected from the group consisting of dogs and cats.

6. The method as set forth in claim 1, wherein the lumen presents an inside diameter and the prosthetic device presents a slightly smaller diameter.

7. The method as set forth in claim 1, wherein said tunica is closed by ligation.

8. A method for neutering a quadruped animal, said method comprising the steps of:
   (a) creating a passageway into the interior of the animal's scrotum which contains a tunica vaginalis, a spermatic cord and a testis by incising the prescrotal skin;
   (b) severing the tunica vaginalis and spermatic cord at a location above the testis;
   (c) removing the testis through said passageway; and
   (d) inserting a prosthetic device through said passageway into the scrotum.

9. The method as set forth in claim 8, and further including the step of:
   (e) repeating steps b, c, and d to remove a second testis and implant a second prosthetic device.

10. The method as set forth in claim 8, the animal being selected from the group consisting of dogs and cats.

11. The method as set forth in claim 8, and further including the step of closing the passageway.

12. A method for neutering a quadruped animal, said method comprising the steps of
   (a) creating a passageway into the interior of the animal's scrotum which contains a tunica vaginalis by incising the prescrotal skin;
   (b) removing a testis through said passageway;
   (c) incising the tunica vaginalis in the lumen thereof;
   (d) inserting a prosthetic device through said passageway and into the lumen of the tunic vaginalis; and
   (e) closing the tunica.

13. The method as set forth in claim 12, wherein the animal's scrotum presents an anterior portion and a posterior portion and the prosthetic device is generally kidney shaped, presenting a convex surface and a concave surface, and further including the step of:
   (e) the prosthetic device being inserted with the convex surface facing the anterior portion of the scrotum and the concave surface facing the posterior portion of the scrotum.

14. A method for neutering a quadruped animal, said method comprising the steps of:
   (a) creating a passageway into the interior of the animal's scrotum;
   (b) removing a testis through said passageway: and
   (c) inserting a prosthetic device through sad passageway and info the scrotum.

15. A method for neutering a quadruped animal, said method comprising the steps of:
   (a) creating a passageway into the interior of a scrotum of said animal which contains a pair of tunica vaginalis, a pair of spermatic cords and a pair of testes by incising the skin in the vicinity of the scrotum;
   (b) the scrotum presenting an anterior portion and a posterior portion;
   (c) incising a first tunica vaginalis in the lumen thereof;
   (d) severing a first spermatic cord and removing a first testis through said passageway;
   (e) providing a first prosthetic device having a generally kidney shape, presenting a convex surface and a concave surface;
   (f) wherein the lumen presents an inside diameter and the prosthetic device presents a slightly smaller diameter;
   (g) inserting said first prosthetic device through said passageway and into the lumen of the first tunica vaginalis;
   (h) the prosthetic device being inserted with the convex surface facing the anterior portion of the scrotum and the concave surface facing the posterior portion of the scrotum;
   (i) closing the first tunica;
   (j) incising the second tunica vaginalis in the lumen thereof;
   (k) severing the second spermatic cord and removing the second testis through said passageway;
   (l) providing a second prosthetic device having a generally kidney shape, presenting a convex surface and a concave surface;
   (m) inserting said second prosthetic device through said passageway and into the lumen of the second tunica vaginalis;
   (n) the second prosthetic device being inserted with the convex surface facing the anterior portion of the scrotum and the concave surface facing the posterior portion of the scrotum;
   (o) closing the second tunica; and
   (p) closing the passageway.

* * * * *